US00PP31913P2

(12) United States Plant Patent
Ackerman et al.

(10) Patent No.: US PP31,913 P2
(45) Date of Patent: Jun. 30, 2020

(54) STRAWBERRY PLANT NAMED 'PE-7.2054'

(50) Latin Name: *Fragaria ananassa*
Varietal Denomination: PE-7.2054

(71) Applicant: PLANT SCIENCES, INC., Watsonville, CA (US)

(72) Inventors: Stephen M. Ackerman, Salinas, CA (US); Steven D. Nelson, Watsonville, CA (US); Michael D. Nelson, Watsonville, CA (US)

(73) Assignee: PLANT SCIENCES, INC., Watsonville, CA (US)

( * ) Notice: Subject to any disclaimer, the term of this patent is extended or adjusted under 35 U.S.C. 154(b) by 0 days.

(21) Appl. No.: 16/501,861

(22) Filed: Jun. 20, 2019

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./156, 208, 209
See application file for complete search history.

*Primary Examiner* — Susan McCormick Ewoldt
*Assistant Examiner* — Karen M Redden
(74) *Attorney, Agent, or Firm* — Foley & Lardner LLP

(57) ABSTRACT

This invention relates to a new and distinct variety of strawberry plant named 'PE-7.2054'. This new strawberry plant named 'PE-7.2054' is primarily adapted to the growing conditions of the central coast of California, and is primarily characterized by its very large fruit size that is conical in shape, with very good flavor and medium to soft flesh; high marketable yield with an early harvest season; medium plant size with dark green, flat to slightly convex foliage; and resistance to *Fusarium* wilt.

4 Drawing Sheets

Latin name of the genus and species of the plant claimed: *Fragaria ananassa.*

Variety denomination: 'PE-7.2054'.

BACKGROUND OF THE INVENTION

The present invention relates to a new and distinct strawberry variety named 'PE-7.2054'. This new variety is a result of a controlled cross made in 2007 in an ongoing breeding program between strawberry variety designated 'PS-5016' (U.S. Plant Pat. No. 17,312), and strawberry selection designated 'PE-1.204' (non-patented). Due to the combining of the reciprocal seed lots, it is unknown as to which parent variety is the seed parent and which parent variety is the pollen parent. The variety is botanically known as *Fragaria ananassa.*

The seedling resulting from the aforementioned cross was selected from a controlled breeding plot in Ventura County, Calif. in the fall of 2009. After its selection, the new variety was asexually propagated by stolons in San Joaquin County, Calif. The new variety was extensively tested over the next several years in fruiting fields in Ventura County, Calif. This propagation has demonstrated that the combination of traits disclosed herein as characterizing the new variety are fixed and remain true to type through successive generations of asexual reproduction.

BRIEF SUMMARY OF THE INVENTION

'PE-7.2054' is primarily adapted to the climate and growing conditions of the central coast of California. The nearby Pacific Ocean provides the needed humidity and moderate temperatures to produce a strong vigorous plant and maintain fruit quality during the fall production months.

The following traits have been repeatedly observed and are determined to be unique characteristics of 'PE-7.2054', which in combination distinguish this strawberry plant as a new and distinct variety:

1. Very large fruit size that is conical in shape, with very good flavor and medium to soft flesh;
2. High marketable yield, with the harvest season considered to be early;
3. Medium plant size, with dark green, flat to slightly convex foliage; and
4. Resistance to *Fusarium* wilt.

The strawberry variety that is believed to be most closely related to the new variety 'PE-7.2054' is 'PE-7.2059' (U.S. Plant Pat. No. 28,756). In side-by-side comparisons to the similar strawberry variety 'PE-7.2059', 'PE-7.2054' differs by the following combination of characteristics as described in Table 1.

TABLE 1

COMPARISON WITH THE STANDARD VARIETY

| Characteristic | 'PE-7.2054' | 'PE-7.2059' (U.S. Plant Pat. No. 28,756) |
|---|---|---|
| Fruit: size | Very large. | Large. |
| Season marketable yield (gm/plt) | 683. | 628. |
| Fruit: insertion of achenes | Level with the surface. | Ranges from level with to above the surface. |
| Fruit: flesh firmness | Ranges from medium to soft. | Medium. |
| Fruit: flavor | Very good. | Good. |
| Time of first fruit | Early. | Medium. |
| Pedicel: pubescence | Medium. | Strong. |
| Pedicel: attitude of hairs | Upward. | Outward. |
| Disease: Fusarium wilt | Resistant. | Susceptible. |

For identification, a series of molecular markers have been determined for this new variety.

'PE-7.2054' differs from its parents, 'PS-5016' and 'PE-1.204', by the following combination of characteristics as described in Tables 2 and 3.

TABLE 2

COMPARISON WITH PARENT A

| Characteristic | 'PE-7.2054' | 'PS-5016' (U.S. Plant Pat. No. 17,312) |
|---|---|---|
| Type of bearing | Everbearing. | Summer bearing. |
| Plant size | Medium. | Large. |
| Fruit size | Large. | Small. |
| Difference between primary and secondary fruit | Ranges from slight to moderate. | Slight. |

TABLE 3

COMPARISON WITH PARENT B

| Characteristic | 'PE-7.2054' | 'PE-1.204' |
|---|---|---|
| Fruit size | Very large. | Medium. |
| Fruit color | Red. | Ranges from orange red to red. |
| Fruit flavor | Very good. | Good. |
| Plant size | Medium | Ranges from medium to small. |

BRIEF DESCRIPTIONS OF THE PHOTOGRAPHS

The accompanying color photographs illustrate the overall appearance of typical specimens of the new strawberry variety 'PE-7.2054', at various stages of development as true as it is reasonably possible with color reproductions of this type. Color in the photographs may differ slightly from the color value cited in the botanical descriptions which accurately describe the color of 'PE-7.2054'. The depicted plant and plant parts of the new strawberry variety 'PE-7.2054' are between three and four months old. The photographs were taken in Ventura County, Calif.:

DETAILED BOTANICAL DESCRIPTION

Figure 1:
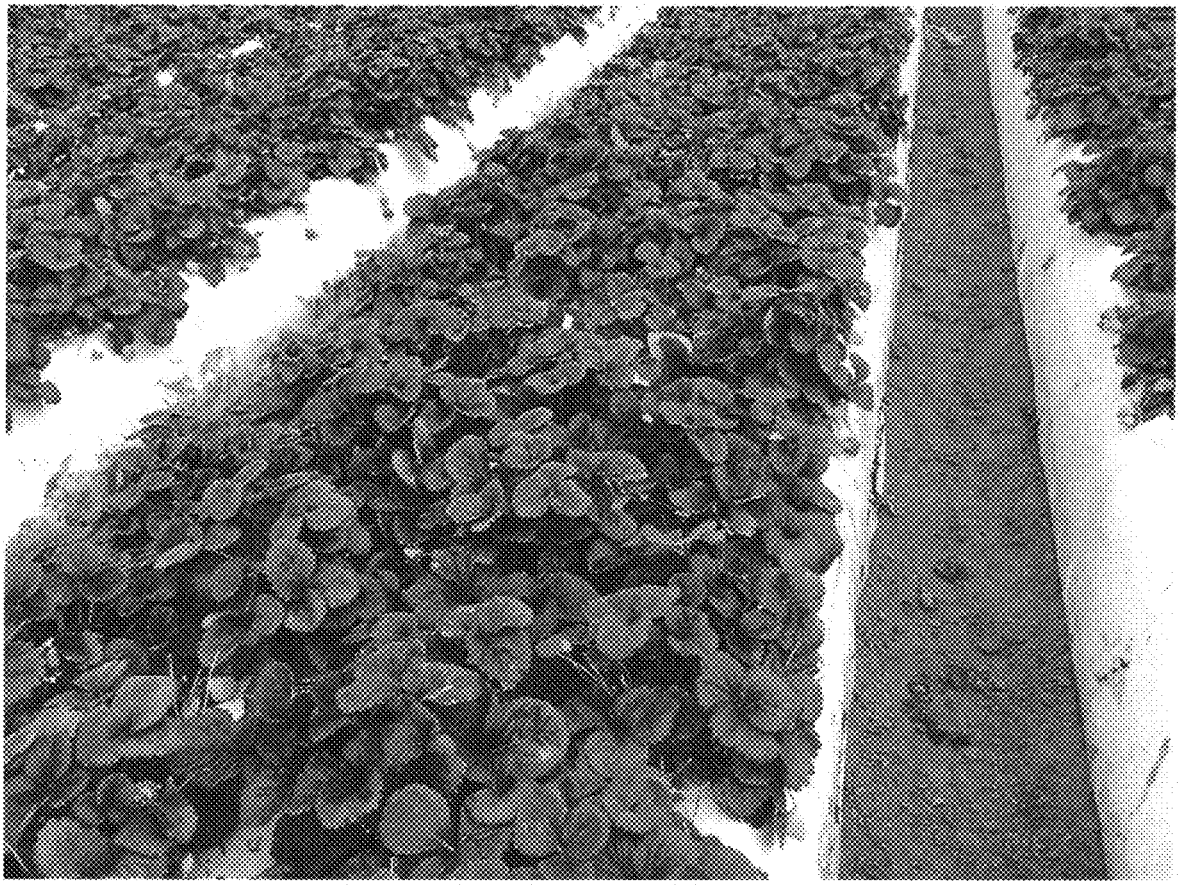
FIG. 1 shows typical fruiting field characteristics of 'PE-7.2054', taken in the month of November.
Figure 2:
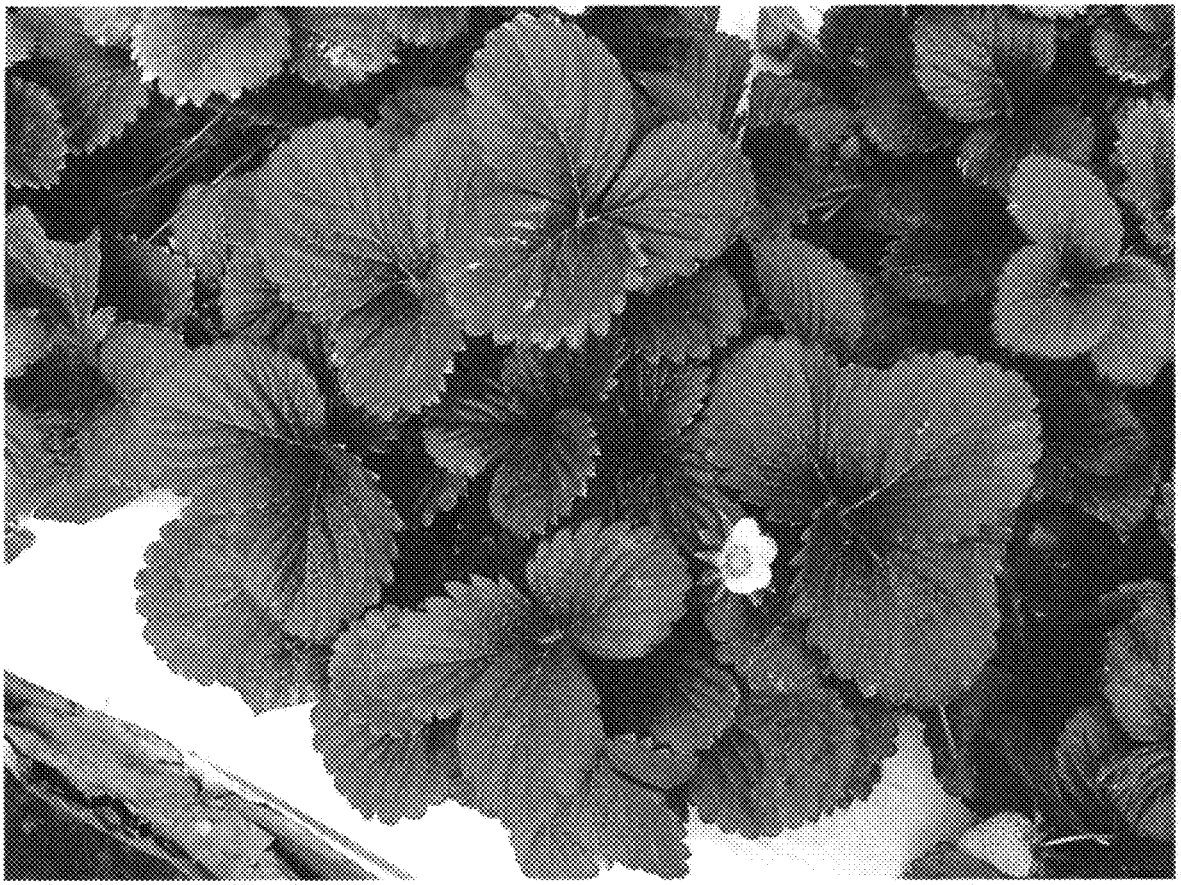
FIG. 2 shows a close-up view of a typical plant of 'PE-7.2054', taken in the month of November.
Figure 3:
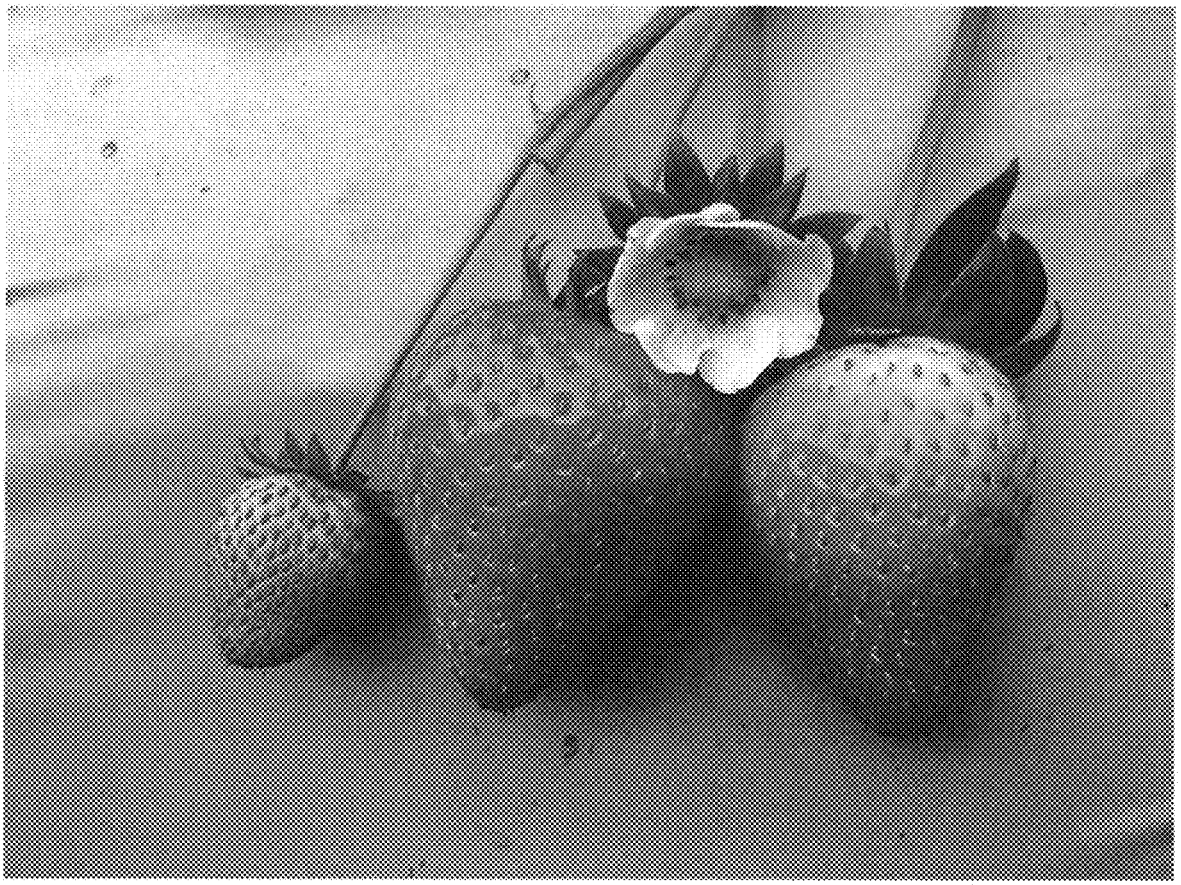
FIG. 3 shows typical mature and immature field fruit of 'PE-7.2054', taken in the month of November.
Figure 4:
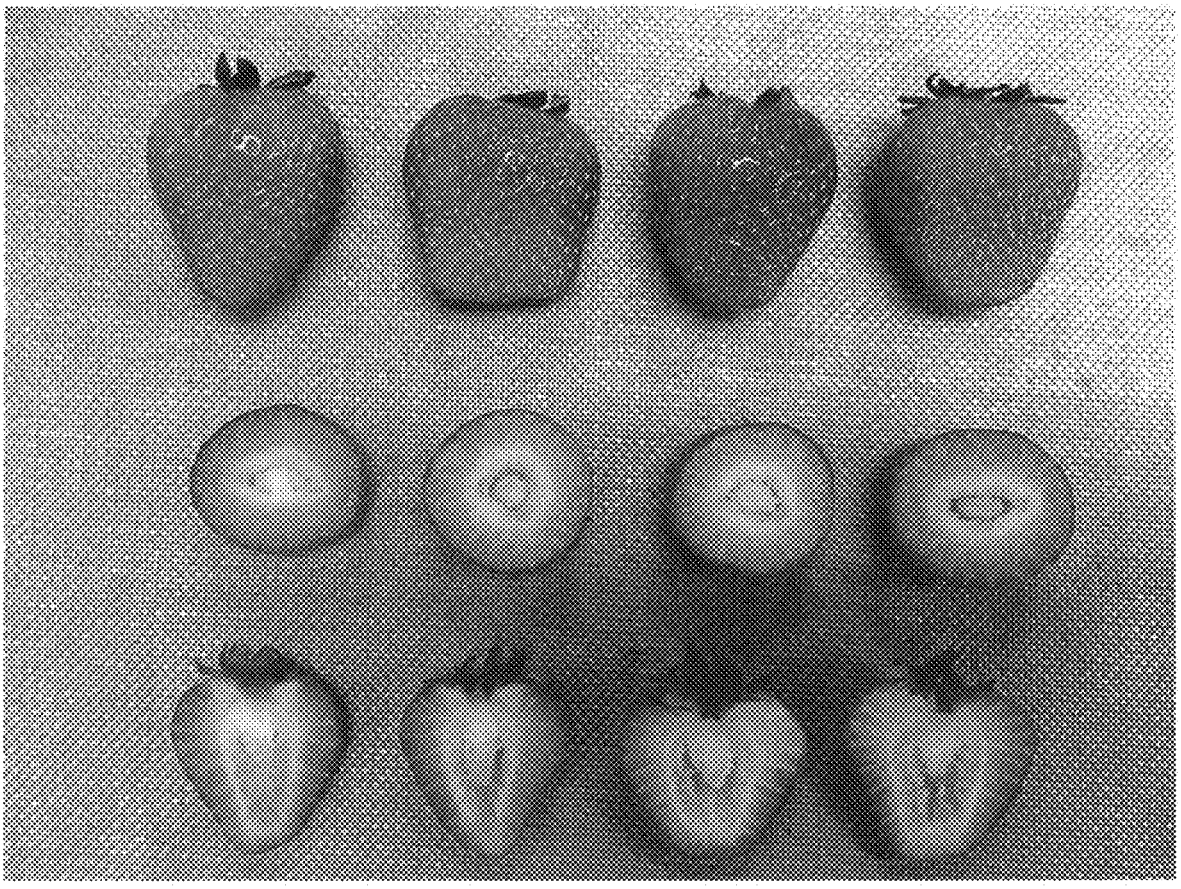
FIG. 4 shows typical internal and external mature fruit characteristics of 'PE-7.2054', taken in the month of November.

The new variety 'PE-7.2054' has not been observed under all possible environmental conditions. The characteristics of the new variety 'PE-7.2054' may vary in detail, depending upon variations in environmental factors, including weather (temperature, humidity and light intensity), day length, soil type and location. In addition, the characteristics of any parental variety or comparison variety included in Tables 1, 2 and 3 of the present invention may vary in detail, depending upon variations in environmental factors, including weather (temperature, humidity and light intensity), day length, soil type and location.

The aforementioned photographs, together with the following description of the new variety 'PE-7.2054', unless otherwise noted, are based on observations taken during the 2018 growing season in Ventura County, Calif. These measurements and ratings were taken from plants of 'PE-7.2054' dug from a low-elevation nursery located in San Joaquin County, Calif. during January 2018 and planted six months later in Ventura County, Calif. The approximate age of the observed plants is four months. Yield observations including average weight and marketable yield, along with fruit quality characteristics including soluble solids, are averaged from six years of data collected from the 2013 through 2018 growing seasons. Flower measurements and characteristics are from secondary flowers unless otherwise noted. Fruit characteristics and measurements are from secondary fruit unless otherwise noted.

Where noted, color terminology follows The Royal Horticultural Society Colour Chart, London (2007).

The following characteristics describe fruit, plant, stolon, foliage, fruiting truss, flower, and pest and disease characteristics of the new strawberry 'PE-7.2054'.

Fruit characteristics:

*Color of mature fruit*.—RHS 46B (red).
*Color of internal flesh*.—RHS 45B (medium red).
*Color of core*.—RHS 44D (light red).
*Average length* (*cm*).—4.3.
*Average width* (*cm*).—3.5.
*Size*.—Large.
*Average length/width ratio*.—1.23 (slightly longer than broad).
*Average calyx diameter* (*cm*).—3.5.
*Average season weight* (*gm*).—24.9.
*Achene color, shaded side*.—RHS 160A (yellow green group).
*Achene color, sun-exposed side*.—RHS 182A (greyed red group).
*Average achene weight* (*mg*).—0.52.
*Average achenes per berry*.—428.
*Season marketable yield* (*gm/plant*).—683.
*Predominant shape*.—Conical.
*Difference in shape between primary and secondary fruit*.—Ranges from slight to moderate.
*Band without achenes*.—Narrow.
*Evenness of surface*.—Even or very slightly uneven.
*Evenness of color*.—Even or very slightly uneven.
*Glossiness*.—Ranges from medium to strong.
*Insertion of achenes*.—Level with surface.
*Position of calyx attachment*.—Inserted.
*Attitude of sepals*.—Ranges from outward to upward.
*Size of calyx in relation to fruit diameter*.—Same size.
*Adherence of calyx* (*when fully ripe*).—Strong.
*Firmness of flesh*.—Ranges from soft to medium.
*Distribution of red color of the flesh*.—Marginal and central.
*Hollow center expression*.—Weak.
*Flavor*.—Very good.
*Average soluble solids* (% *brix*).—8.2.
*Time of first flowering*.—Early (August in Ventura County, Calif.).
*Time of first harvesting*.—Early (September in Ventura County, Calif.).
*Harvest period*.—Late September to mid-December (in Ventura County, Calif.).

*Harvest maturity*.—Early season (October in Ventura County, Calif.).
*Type of bearing*.—Fully remontant (non-flowering runners).

Plant characteristics:
*Average height* (*cm*).—21.0.
*Average spread* (*cm*).—37.0.
*Size*.—Medium.
*Habit*.—Upright.
*Density*.—Medium.
*Vigor*.—Strong.

Stolon characteristics:
*Color*.—RHS 146C (yellow green group).
*Anthocyanin coloration*.—RHS 183C (greyed red group).
*Anthocyanin intensity*.—Medium.
*Pubescence*.—Medium.
*Attitude of hairs*.—Upward.
*Average quantity in nursery* (*per sq. ft.*).—5-6 (ranges from few to medium).
*Average diameter at bract* (*mm*).—3.6 (ranges from medium to thick).

Terminal leaflet characteristics:
*Average length* (*cm*).—8.3.
*Average width* (*cm*).—7.5.
*Length/width ratio*.—1.11 (longer than broad).
*Shape of base*.—Acute.
*Margins* (*shape of teeth*).—Obtuse (serrate to crenate).
*Serrations per leaf*.—21.9.

Foliage characteristics:
*Color of upper surface*.—RHS N137A (dark green).
*Color of underside*.—RHS 147C (yellow green group).
*Number of leaflets*.—3.
*Size*.—Medium.
*Average area terminal* ($cm^2$).—61.5.
*Average length* (*cm*).—12.7.
*Average width* (*cm*).—16.3.
*Average area foliage* ($cm^2$).—208.
*Shape in cross section*.—Flat to slightly convex.
*Interveinal blistering*.—Medium.
*Leaf glossiness*.—Ranges from medium to strong.
*Leaf variegation*.—Absent.

Petiole characteristics:
*Color*.—RHS 146D (yellow green group).
*Average length* (*cm*).—16.1.
*Average diameter* (*mm*).—3.3.
*Attitude of hairs*.—Slightly outward.
*Frequency of bract leaflets*.—Occasionally.
*Bract leaflet size*.—Small.
*Pubescence*.—Sparse.
*Petiolule color*.—RHS 146D (yellow green group).
*Petiolule average length* (*mm*).—10.8.

Stipule characteristics:
*Color*.—RHS 146D (yellow green group).
*Anthocyanin coloration*.—No coloration observed.
*Anthocyanin intensity*.—Absent or very weak.
*Average length* (*mm*).—13.9.
*Average width* (*mm*).—9.5.

Fruiting truss characteristics:
*Anthocyanin coloration*.—RHS 181C (greyed red group).
*Anthocyanin intensity*.—Absent or very weak.
*Average length at maturity* (*cm*).—24.6.
*Position relative to foliage*.—Ranges from beneath to level with.
*Season average number of flowers per plant*.—25-30 (ranges from medium to many).
*Pedicel attitude of hairs*.—Upward.
*Pubescence*.—Medium.
*Attitude at first pick*.—Prostrate.

Flower characteristics:
*Petal color*.—RHS NN 155C (white group).
*Sepal color*.—RHS 137A (green group).
*Average corolla diameter* (*mm*).—33.0 (large).
*Average calyx diameter* (*mm*).—37.0.
*Average petal length* (*mm*).—12.8.
*Average petal width* (*mm*).—11.8.
*Average petal length/width ratio*.—1.08 (longer than broad).
*Average petals per flower*.—7.1.
*Average sepal length* (*mm*).—13.7.
*Average sepal width* (*mm*).—5.3.
*Average sepal length/width ratio*.—2.6.
*Average sepals per flower*.—13.6.
*Size of calyx relative to corolla*.—Larger.
*Size of inner calyx relative to outer calyx*.—Same.
*Relative position of petals* (*flowers with* 5-6 *petals*).—Overlapping.

Reproductive organs:
*Receptacle/ovary color*.—RHS 148B (yellow green group).
*Anther/pollen color*.—RHS 15A (yellow group).
*Stamen*.—Present.
*Pollen amount*.—Abundant.

Pest and disease reactions:
*Powdery mildew* (*sphaerotheca macularis*).—Moderately susceptible.
*Botrytis fruit rot* (*botrytis cinerea*).—Moderately susceptible.
*Fusarium wilt* (*fusarium oxysporum*).—Resistant.
*Anthracnose crown rot* (*colletotrichum fragariae*).—Moderately susceptible.
*Two-spotted spider mite* (*tetranychus urticae*).—Moderately susceptible.

We claim:

1. A new and distinct strawberry plant named 'PE-7.2054', as herein described and illustrated by the characteristics set forth above.

* * * * *